(12) United States Patent
Salmon et al.

(10) Patent No.: US 9,468,793 B2
(45) Date of Patent: Oct. 18, 2016

(54) SYSTEM FOR MONITORING FITNESS PERFORMANCE

(71) Applicants: D'Miles Salmon, Jacksonville, OR (US); David Stubben, Cameron Park, CA (US)

(72) Inventors: D'Miles Salmon, Jacksonville, OR (US); David Stubben, Cameron Park, CA (US)

( * ) Notice: Subject to any disclaimer, the term of this patent is extended or adjusted under 35 U.S.C. 154(b) by 167 days.

(21) Appl. No.: 13/987,692

(22) Filed: Aug. 22, 2013

(65) Prior Publication Data
US 2014/0235409 A1 Aug. 21, 2014

Related U.S. Application Data

(60) Provisional application No. 61/796,522, filed on Nov. 13, 2012, provisional application No. 61/855,673, filed on May 21, 2013, provisional application No. 61/957,758, filed on Jul. 12, 2013.

(51) Int. Cl.
| | | |
|---|---|---|
| *A63B 71/00* | (2006.01) | |
| *A63B 21/00* | (2006.01) | |
| *A63B 21/072* | (2006.01) | |
| *A63B 71/06* | (2006.01) | |
| *A61B 5/22* | (2006.01) | |

(52) U.S. Cl.
CPC ....... *A63B 21/0724* (2013.01); *A63B 21/0628* (2015.10); *A61B 5/224* (2013.01); *A63B 71/0619* (2013.01); *A63B 2220/17* (2013.01); *A63B 2220/30* (2013.01); *A63B 2220/40* (2013.01); *A63B 2220/52* (2013.01); *A63B 2220/803* (2013.01); *A63B 2220/805* (2013.01); *A63B 2220/89* (2013.01); *A63B 2225/20* (2013.01); *A63B 2225/50* (2013.01)

(58) Field of Classification Search
CPC .... A63B 21/00; A63B 21/06; A63B 21/062; A63B 21/0623; A63B 21/0626; A63B 21/0724; A63B 24/00; A63B 24/0062; A63B 24/0065; A63B 24/0068
USPC ...................................... 482/1, 8, 9, 92–104
See application file for complete search history.

(56) References Cited

U.S. PATENT DOCUMENTS

| | | | | |
|---|---|---|---|---|
| 5,655,997 | A * | 8/1997 | Greenberg ......... | A63B 21/0628 482/1 |
| 6,231,481 | B1 * | 5/2001 | Brock ................... | A63B 21/072 482/8 |
| 6,494,811 | B1 * | 12/2002 | Alessandri ......... | A63B 21/0628 482/8 |
| 6,539,336 | B1 * | 3/2003 | Vock .................... | A42B 3/0433 702/178 |
| 7,357,765 | B1 * | 4/2008 | Watson ............ | A63B 21/00072 482/142 |
| 7,455,621 | B1 * | 11/2008 | Anthony ............. | A63B 21/0724 482/3 |
| 7,473,211 | B2 * | 1/2009 | Lee .................... | A63B 21/0628 482/94 |

(Continued)

*Primary Examiner* — Stephen Crow
*Assistant Examiner* — Garrett Atkinson
(74) *Attorney, Agent, or Firm* — James A. Gavney, Jr.; JAG Patent Services

(57) ABSTRACT

A workout system for monitoring fitness and generating a workout summary is disclosed. The system includes a workout module that integrates with weight lifting equipment. The workout module includes one or more motion detectors that detect repetitions and/or tempo of weights lifted or displaced and a computer that logs and stores the repetitions and/or the tempo that weights are lifted or are displaced. The workout module also preferably includes a resistance, a radio frequency, an optical or a magnetic weight sensor or reader that automatically reads and determines values of weights used in the workout. The workout module also preferably includes a radio transmitter to transmit workout data and workout parameters to a remote computing device.

16 Claims, 4 Drawing Sheets

(56) References Cited

U.S. PATENT DOCUMENTS

| | | | | |
|---|---|---|---|---|
| 7,771,319 B1* | 8/2010 | Spoeth, Jr. | ............ | A63B 21/152 482/8 |
| 7,909,741 B2* | 3/2011 | Kim | ................. | A63B 21/065 482/107 |
| 8,105,207 B1* | 1/2012 | Lannon | ............ | A63B 23/03566 482/1 |
| 8,337,365 B2* | 12/2012 | Kim | ................. | A63B 21/065 482/8 |
| 8,529,408 B2* | 9/2013 | Bell | ............... | A63B 21/00069 482/8 |
| 8,990,048 B2* | 3/2015 | Czaja | ................. | A63C 9/00 422/63 |
| 2003/0032529 A1* | 2/2003 | Alessandri | ............ | A63B 24/00 482/94 |
| 2008/0242512 A1* | 10/2008 | Kim | ................. | A63B 21/065 482/8 |
| 2011/0218455 A1* | 9/2011 | Hennig | ............... | A63B 71/085 600/553 |
| 2011/0287896 A1* | 11/2011 | Kim | ................. | A63B 21/065 482/8 |
| 2013/0041617 A1* | 2/2013 | Pease | ................. | A43B 3/0005 702/139 |
| 2014/0031172 A1* | 1/2014 | Chen | ................. | A63B 21/0628 482/5 |
| 2014/0248996 A1* | 9/2014 | Adel | ................. | A63B 24/0062 482/8 |
| 2014/0256516 A1* | 9/2014 | Calderone | ............. | A61B 5/103 482/98 |

\* cited by examiner

SYSTEM FOR MONITORING FITNESS PERFORMANCE

RELATED APPLICATIONS

This Application claims priority under 35 U.S.C. §119(e) from the Co-pending U.S. Provisional Patent Application Ser. No. 61/796,522, filed on Nov. 13, 2012, and titled "EXERCISE MONITORING DEVICE", the Co-pending U.S. Provisional Patent Application Ser. No. 61/855,673, filed on May 21, 2013, and titled "APPARATUS FOR MEASURING, GUIDING AND RECORDING FITNESS PERFORMANCE " and the Co-pending U.S. Provisional Patent Application Ser. No. 61/957,758, filed on Jul. 12, 2013, and titled "APPARATUS FOR MEASURING, GUIDING AND RECORDING FITNESS PERFORMANCE " the contents of which are all hereby incorporated by reference.

FIELD OF THE INVENTION

This invention relates generally to systems for monitoring fitness performance. More specifically, this invention relates to a system for monitoring repetitive load-bearing displacements while using exercise equipment.

BACKGROUND OF THE INVENTION

Within the physical fitness equipment industry, there are many workout programs available that provide feedback regarding data of workout routines and networking capabilities displayed on digital media screens. These current systems work well with cardiovascular equipment such as spin bikes, treadmills, and elliptical machines that already have digital media screens.

There are also a number of fitness watches and heart monitoring devices that are currently available. These devices record your heart rate, record your workout time, record the distances of runs or bike rides, create programs to maximize your training and even map workout pathways.

Weight lifting equipment includes, for example, weight machines that require a user to insert a pin in a column of weight plates to select the weight amount (pin selectable weight machines (PSWM)), fixed weight free weights (FWFW), such as dumbbells, barbells and kettle weights, in which the weight is a set amount, variable weight free weights (VWFW), such as dumbbells and barbells in which plates are mounted to vary the weight amount, plate weight loaded equipment (PWLE), in which the machine controls the motion track of the exercise but the weight is determined by loading plates onto the machine and resistive spring or resistive pulley machines where weight is simulated by the spring and/or pulley. While some of these type of weight lifting equipment have counters for keeping track of the number of repetitions that a selected weight or resistance is displaced, none of these prior art device are capable of measuring, guiding, or recording fitness performance while using weight lifting equipment.

SUMMARY OF THE INVENTION

The present invention is directed to a system for monitoring fitness. The system includes a workout module that is preferably portable and configured to be used with a variety of weight lifting equipment. The workout module includes a control unit with a detecting unit (motion detector) and computing unit (micro-processor and memory).

The control unit, along with all of the necessary software, logs and stores displacements of loads from the weight lifting equipment to provide a workout summary. The detecting unit communicates one or more of a number (repetitions) and a frequency (tempo) of the displacements of loads to the computing unit. The computing unit logs and stores the repetitions and/or tempo of the displacements of the loads to generate the workout summary. The detecting unit preferably includes one or more accelerometers to detect the repetitions and/or the tempo of the displacements. However, other types of motion sensors including, but not limited to, optical motion sensors, acoustic motion sensors and combinations thereof are contemplated.

In yet further embodiments of the invention, the workout module includes a display and/or audio output for indicating a selected or preferred tempo of the displacements of the loads and/or a completion of a selected or preferred number of displacements the loads.

The workout module also includes an input unit for entering values of loads into the computing unit. For example, the workout module includes a user interface to manually input the values of the loads. Preferably, the workout module includes a mechanism for automatically reading and determining values of the loads. For example, the workout module includes an input unit with a sensor that includes a resistance measuring circuit. The resistance measuring circuit reads an indicator or indicator decal on a portion of the weight lifting equipment to determine the values of loads used during workouts. In accordance with this embodiments of the invention weights are equipped with conductive ink decals that code for the values of the loads. Alternatively, the input unit includes a radio frequency measuring circuit and weights are equipped with one or more radio frequency identification devices that code for the values of loads. It will be clear to one skilled in the art that input units with other sensors for determining values of loads are within the scope of the invention. For example, loads are coded with optical decals or magnetic decals and the sensor is an optical reader or magnetic reader that determines the values of the loads from the optical decals.

In accordance the embodiments of the invention a workout module includes a control module with a micro-processor, memory, user interface and display for inciting modes of operation, such as described in detail below. The workout module also includes a weight sensing pin that is in electrical communication with the control module. The weight sensing pin is configured for securing to selected loads on weight lifting equipment. The securing pin is equipped with a sensor (input unit) that reads indicators corresponding to the selected loads and communicates values of the selected loads to the computing unit. The values of the selected loads communicated to the computing unit of control module are then used for generating the workout summary. In accordance with the embodiments of the invention, the control module and the weight sensing pin detachably couple together and the weight sensing pin includes a battery unit for powering the control module and sensor. As described above, the sensor is a resistance sensor, a radio frequency sensor, an optical sensor and/or magnetic sensor.

In still further embodiments the invention, a workout module include a transmitter unit for down loadings workout parameters or transmitting workout summaries to a remote computing device. The transmitter unit includes, for example, a wireless transmitter or connection (USB or ethernet chord) that allows the workout module to communicate with a personal commuter, a smart phone, or other computing device. Where the transmitter unit includes a wireless transmitter, the transmitter is preferably a radio transmitter that transmits signals over remote network or over a peer-to peer network, such as bluetooth devices.

DETAILED DESCRIPTION OF THE INVENTION

Figure 1:
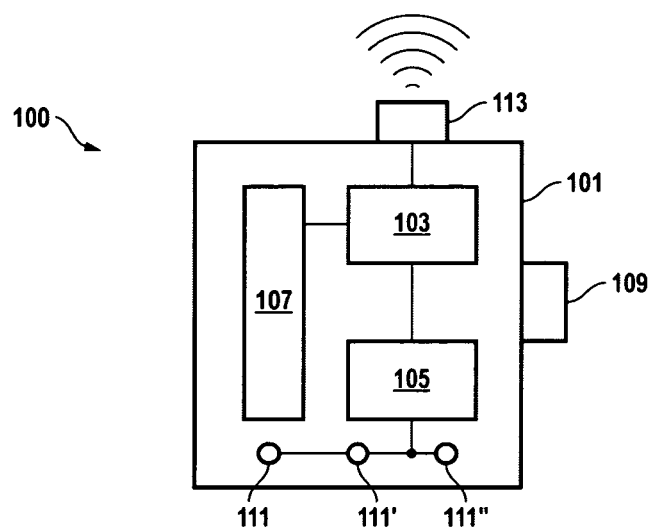
FIG. 1 illustrates a schematic representation of a system for monitoring fitness, in accordance with the embodiments of the invention.

FIG. 1 shows a system 100 for monitoring fitness. The system 100 includes a workout module 101 that is preferably portable and configured to be used with a variety of weight lifting equipment. The workout module 101 includes a control unit with a detecting unit (motion detector) 103 and computing unit (micro-processor and memory) 105.

The computing unit 105 runs all of the necessary software to log and store displacements of loads from the weight lifting equipment to provide or generate a workout summary. The detecting unit 103 communicates repetitions (number) and/or frequency (tempo) of the displacements of the loads to the computing unit 105.

Still referring to FIG. 1, the detecting unit 105 preferably include one or more accelerometers to detect the repetitions and/or the frequency of the displacements, however, other types of motion sensors including, but not limited to, optical motion sensors, acoustic motion sensors and combinations thereof are contemplated.

In yet further embodiments of the invention, the workout module 101 includes a display and/or audio output 111, 111' and 111" for indicating a selected or preferred tempo of the displacements of loads and/or completion of a selected or preferred number of displacements the loads. The display and/or audio output 111, 111' and 111" also indicates, for example, modes of operation of the workout module 101, such as on and off.

The workout module 100 also includes an input unit 107 for entering values of loads into the computing unit 103. For example, the workout module 101 includes a user interface to manually input the values of the loads. Preferably, the workout module 101 includes a mechanism for automatically reading and determining values of the loads. For example, the workout module 101 includes an input unit 101 with a sensor that includes a resistance measuring circuit (not shown). The sensor and resistance measuring circuit read an indicator or indicator decal on a portion of the weight lifting equipment, such as described with reference to FIGS. 3A-B, to determine the values of loads used during workouts.

In accordance with further embodiments of the invention the workout module 101 includes a an attachment feature 109 for attaching to a portion of the user's body or a portion of the weight lifting equipment. For example, the attachment feature 109 is a clip, a strap, a pin and or any other suitable attachment feature.

In still further embodiments the invention, a workout module 101 include a transmitter unit 113 for down loading workout parameters or transmitting workout summaries to a remote computing device (not shown). The transmitter unit 113 includes, for example, a wireless transmitter or connection (USB or ethernet chord) that allows the workout module to communicate with remote computing device, such as a personal commuter, a smart phone, or any other computing device. Where the transmitter unit 113 includes a wireless transmitter, the wireless transmitter is preferably a radio transmitter that transmits signals over remote network or over a peer-to peer network, such as bluetooth devices.

Figure 2:
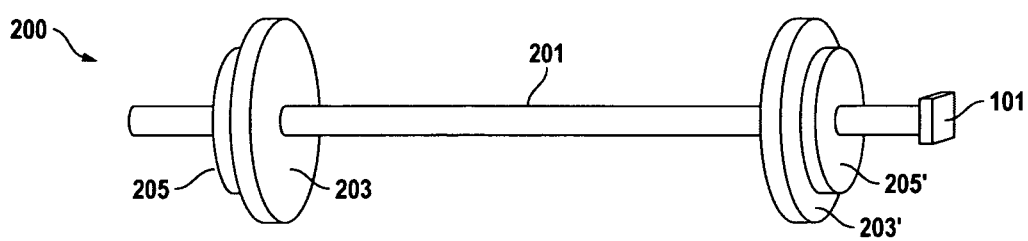
FIG. 2 illustrates a system for monitoring fitness attached to a set of free weights, in accordance with the embodiments of the invention.

Referring now to FIG. 2, in operation the workout module 101 is attached to weight equipment. The weight equipment 200 includes, for example, a weight bar 201 and free weights 203, 203', 205 and 205'. In this example, the workout module 101 is attached to an end portion of the weight bar 201. However, as stated above, the workout module 101 can also be configured to attach to a portion of a user's body. In operation the workout module 101 counts the number of times or repetitions and/or the rate or the tempo that the weight bar 201 and the free weights 203, 203', 205 and 205' are lifted. Preferably, the workout module 101 registers the amounts or values of the weight bar 201 and the free weights 203, 203', 205 and 205' either by having the amounts or values manually entered into the input unit 107 (FIG. 1) or, as described below, by having the values automatically entered into the input unit 107 by via sensor mechanism.

Figure 3A:
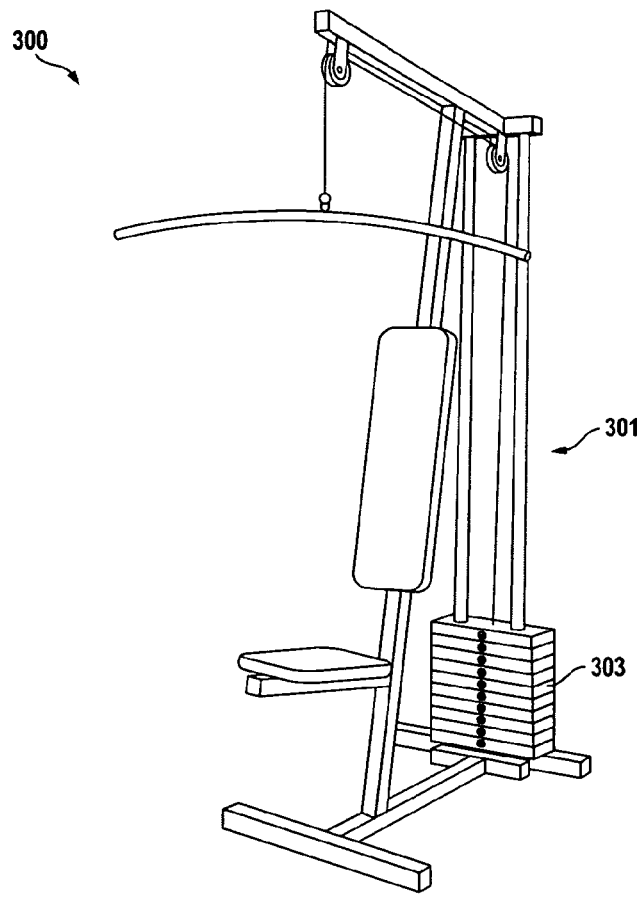
FIG. 3A illustrates weight lifting equipment with selectable free weights coded with an indicator, in accordance with the embodiments of the invention.
Figure 3B:
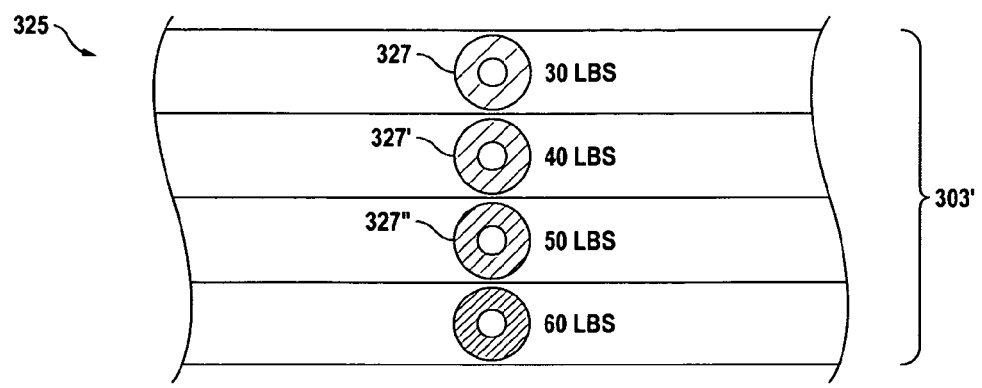
FIG. 3B shows an exploded view of free weights coded with an indicator, in accordance with the embodiments of the invention.

Referring now to FIG. 3, weight equipment 300 includes a pulley mechanism 301 attached to a set of weights 303. In accordance with this embodiments of the invention, the set of weights 303 include indicator decals or markings that code for the values of the loads of the set of weights, such as described with reference to FIG. 3B.

FIG. 3B shows an exploded view 325 of a section 303' of the set of weights 303. The section weights 303' are equipped with conductive ink decals 327, 327' and 327" that code for the values of the loads. The loads are set by placing a weight sensing pin 400 (FIG. 4) in a selected slot or hole.

In yet further embodiments of the invention, the workout module 101 (FIG. 1) is configured to attached to a portion of a pulley mechanism 301, such as a pulley wheel or cable. In operation the workout module 101 detects and/or monitor distance of displacement of selected weights from the set of weights 303, repetitions of displacement of displacement of selected weights from the set of weights 303 and/or frequency of displacement of selected weights from the set of weights 303.

Figure 4A:
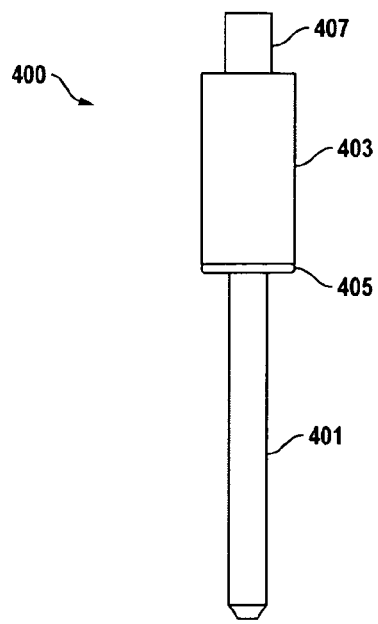
FIG. 4A illustrates a weight sensing pin for reading weight values, in accordance with the invention.

Referring to FIG. 4A, a workout module 427 (FIG. 4C) includes a weight sensing pin 400. The weight sensing pin 400 includes a pin structure 401 for placing into a hole or slot and securing a selected portion of weights from the set of weights 303 (FIG. 3A). The weight sensing pin 400 includes a sensor 405, a battery 403 and coupling mechanism 407 for detectably coupling to a control module 425 (FIG. 4B) and for placing the weight sensing securing pin 400 in electrical communication with the control module 425.

Figure 4B:
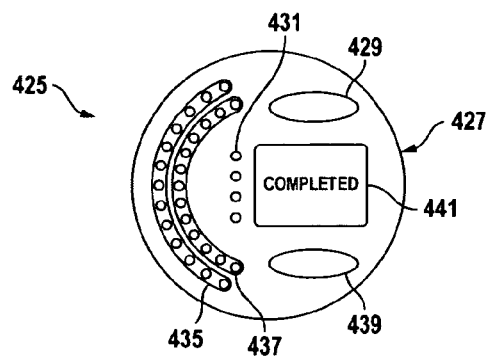
FIG. 4B illustrates a control module with a motion sensor and computing unit for coupling to the a weight sensing pin, in accordance with the embodiments of the invention.

Referring to FIG. 4B, the control module 425 includes a number of user interfaces. For example, the control module 425 includes a status display 441, a setting button 429, an on/off button 439 and one or more sets or arrays of LED's 435 and 437. For example, a first set or array of LED's 435 displays a selected number of repetitions for a weight lifting workout and a second set or array of LED's 437 simultaneously displays a number repetitions of the weight lifting workout completed by a user. In further embodiments of the invention the control module 425 includes audio output or display that indicates a selected, preferred tempo of a weight lifting workout and/or a actual tempo of a weight lifting workout.

Figure 4C:
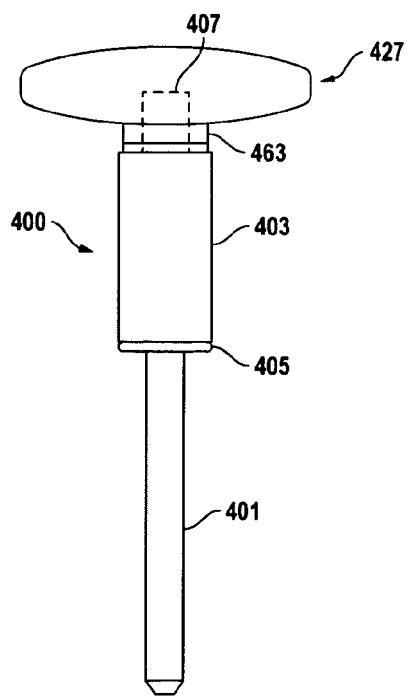
FIG. 4C illustrates a workout module with a control module detachably coupled to a weight sensing pin, in accordance with the embodiments of the invention.

FIG. 4C shows the workout module 427 with the weight sensing pin 400 electrically coupled to the control modules 427 through a connection 463 and the coupling mechanism 407. With the weight sensing pin 400 electrically coupled to the control modules 427, the battery 403 supplies power to the control module 427. The sensor 405 reads indicators corresponding to selected loads from the set of weights 303 (FIG. 3A) and communicates the values of the selected loads to a computing unit in the control module 427, via a sensing circuit 451 (FIG. 4D).

In accordance with this embodiments of the invention weights 303 (FIG. 3A) are equipped with conductive ink decals 327, 327' and 327" (FIG. 3B) that code for the values of the loads. In operation, the pin structure 401 of the weight sensing pin 400 is placed in a selected slot or hole on the set of weights 303. The sensor 405 senses conductive ink decals 427, 427' and 427" and transmits a signals to resistance measuring circuit on a printed circuit 451 (FIG. 4D) that is in electrical communication with a micro-processor 453 for determining the selected load. The control module 427 then counts the number or times or repetitions and/or the rate or the tempo that the selected portion of the set of weights 303 are displaced via a motion detector 457 (FIG. 4D) to generate a workout summary. In further embodiments of the loads are coded radio frequency identification device or decals, optical decals or magnetic decals and the sensor 405 is an radio frequency reader, an optical reader or a magnetic reader that determines the values of the loads from the optical decals or magnetic decals and an appropriates sensing circuit.

Figure 4D:
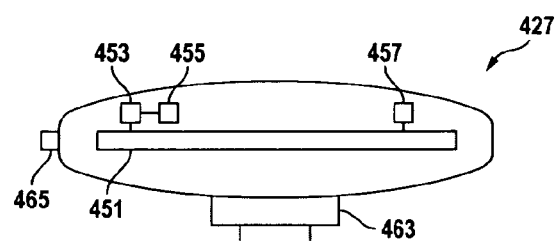
FIG. 4D shows a cross-sectional view of a control module with a motion sensor, a computing unit and wireless transmitter, in accordance with the invention.

FIG. 4D shows a cross-sectional view of the control module 427. The control module 427 includes a micro-processor 453 and memory unit 455 for computing and storing workout data and parameters. The control module 427 also includes a motion sensor 457 for sensing displacements of selected loads of weight from the weight lifting equipment, such as described above. The control module 427 also includes all of the necessary circuitry 451 providing electrical contacts between the micro-processor 453, the motion detector 457, sensor 405 and the user interfaces, described with reference to FIG. 4B. The circuitry 451 includes, for example, the resistance measuring circuit determine loads from the sensor 405, such as described above. The control module 427 also includes a wireless transmitter 465 for transmitting workout data and workout parameters to a remote computing device, such as described above.

Figure 5:
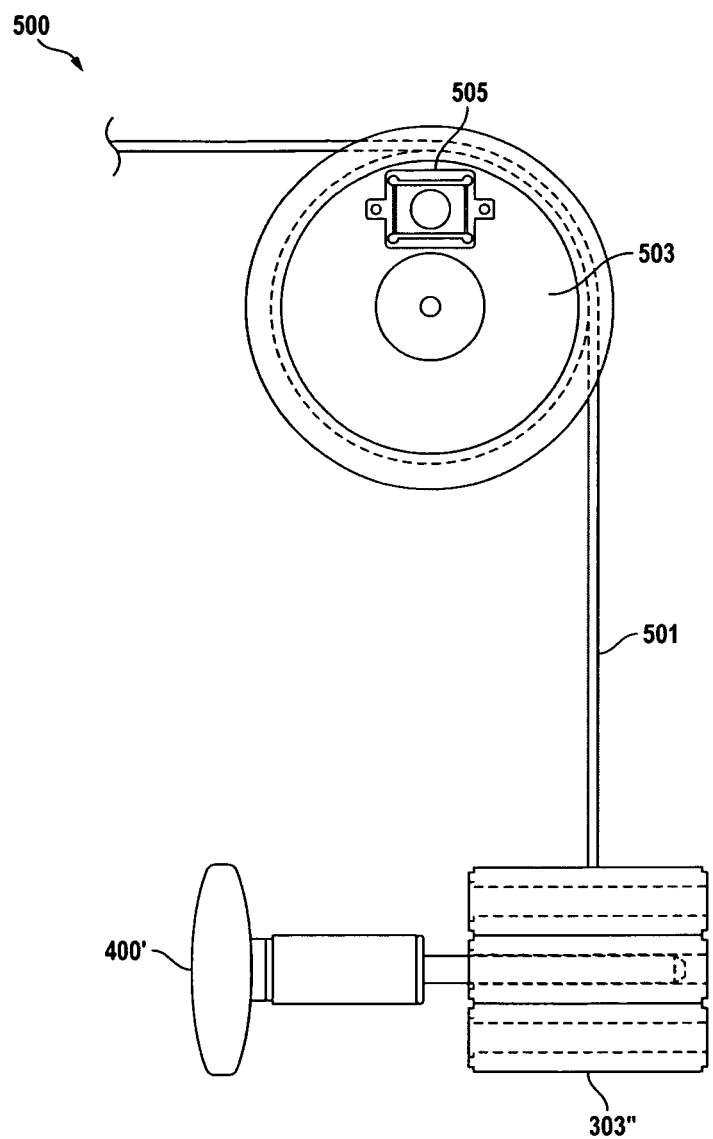
FIG. 5 illustrates a system for monitoring fitness with a weight sensing pin and a kinetic sensor module, in accordance with the invention.

In accordance with further embodiments of the invention a system for monitoring fitness 500 includes a sensing pin 400' and a kinetic sensing control module 505, as shown in FIG. 5. The sensing pin 400' includes all or any portion of the electrical or mechanical components of the weight sensing pin 400 described with reference to FIGS. 4A-D. The sensing pin 400' is configured to couple to, for example, a set of weights 303" or any other portion of a piece of workout equipment. The sensing pin 400' is configured to detect a selected load and/or identify the piece of workout equipment, such as described above with reference to FIGS. 3A-B. The kinetic sensing control module 505 is couple to a pulley 503, a cable 501 or any other kinetic point (moving part) of the piece of workout equipment. The kinetic sensing control module 505 includes a motion sensor, such as an accelerometer, that measures, monitors or counts the number of times or repetitions and/or the rate or the tempo that the selected load is displaced during a workout session. In addition, the kinetic sensing control module 505 is capable of monitoring or measuring distances that the selected load is displaced during exercise repetitions of the workout session. The kinetic sensing control module 505 includes a micro-processor and radio transmitter that transmits workout data to the sensing pin 400" to provide a workout summary corresponding to the piece of workout equipment that the kinetic sensing control module 505 is coupled to or attached to. During a workout routine, the sensing pin 400" is moved to other pieces of workout equipment that includes a kinetic sensing control module 505, such as described above. to provide a workout summary for each piece of workout equipment used throughout the workout session.

Still referring to FIG. 5, the sensing pin 400' identifies the piece of workout equipped being used and/or the selected load with a reader that reads an optical or magnetic decal, such as described above. Alternatively, or in addition to using a reader and an optical or magnetic decal, the sensing pin 400" identifies the piece of workout equipped being used by an identifier or address that is broadcast by the kinetic sensing control module 505 using the radio transmitter. In further embodiments of the invention, the sensing pin 400' includes an impact sensor, such that the sensing pin 400 turns on when the selected load is moved and turns off after a period of time that the impact sensor no longer detects contact. Alternatively, the sensing pin 400' and/or the kinetic sensing control module 505 are tuned on when motion is detected by a motion sensor and then shut off after a period of time when motion is no longer detected by either or both of the sensing pin 400 and the kinetic sensing control module 505.

The present invention has been described in terms of specific embodiments incorporating details to facilitate the understanding of the principles of construction and operation of the invention. As such, references, herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A portable system for monitoring fitness comprising a workout module, the workout module comprising:
  a) a computing unit with a micro-processor and memory for running software that analyzes a workout from displacements of a load from weight lifting equipment with a plurality of weights, wherein each of the plurality of weights has a unique indicator decal attached thereto;
  b) an input unit for entering the load into the computing unit;

c) a detecting unit with a motion detector that is in electrical communication with the computing unit for counting displacements of the load;
d) an output unit for providing a summary of the workout, wherein the input unit for entering the load into the computing unit includes a sensor that automatically determines the load by reading the unique indicator decal coded for a value of the load, when the sensor is placed in the proximity of the unique indicator decal; and wherein the sensor includes a measuring circuit for reading the unique indicator decal, wherein the unique indicator decal is a radio frequency indicator decal (RFID) or a conductive ink decal.

2. The system of claim 1, wherein the workout module includes an attachment feature for attaching to a portion of the user's body or a portion of the weight lifting equipment.

3. The system of claim 1, wherein the motion sensor includes one or more accelerometers.

4. The system of claim 1, further comprising transmitter unit for down loading the summary of the workout to a remote computing device.

5. The system of claim 4, wherein the transmitter unit includes a radio transmitter.

6. The system of claim 1, wherein the detector unit further counts a tempo of the displacements of the load.

7. The system of claim 1, further comprises an audio output for indicating a selected tempo of the displacement of the load and completion of a selected number of displacements the load.

8. A system for monitoring fitness comprising:
a) a portable control module with a motion detector and computing unit, wherein the motion sensor and computing unit logs and stores displacements of a selected load to provide a workout summary; and
b) a weight sensing pin in electrical communication with the portable control module for securing to the selected load on weight lifting equipment with a plurality of weights, wherein each of the plurality of weights has a unique conductive ink or radio frequency indicator decal attached thereto, wherein the weight sensing pin includes a sensor that reads the unique conductive ink or radio frequency indicator decal coded for a value of the selected load, when the sensor is placed in the proximity of the unique conductive ink or radio frequency indicator decal and communicates a value of the selected load to the computing unit of the portable control module for computing the workout summary.

9. The system of claim 8, wherein the motion detector includes one or more accelerometers.

10. The system of claim 8, wherein the sensor that reads the indicator decal includes a resistance measuring circuit for reading the unique conductive ink indicator decal.

11. The system of claim 8, wherein the sensor that reads the unique conductive ink or radio frequency indicator decal further includes a radio frequency measuring circuit for sensing one or more one or more radio frequencies.

12. The system of claim 8, further comprising transmitter unit for down loading the workout summary to a remote computing device.

13. The system of claim 12, wherein the transmitter unit includes a radio transmitter.

14. The system of claim 8, wherein the motion sensor and computing unit further logs and stores a tempo of the displacements of the selected load.

15. The system of claim 8, further comprises an audio output for indicating a preferred tempo of the displacements of the selected load.

16. The system of claim 8, wherein the weight sensing pin includes a battery unit for powering portable control module.

* * * * *